United States Patent [19]

Shimbo et al.

[11] Patent Number: 4,724,262
[45] Date of Patent: Feb. 9, 1988

[54] PROCESS FOR PURIFYING L-ASCORBIC ACID 2-PHOSPHATE

[75] Inventors: Kuniaki Shimbo; Nobuyuki Nagato; Isamu Taguchi, all of Kanagawa, Japan

[73] Assignee: Showa Denko Kabushiki Kaisha, Tokyo, Japan

[21] Appl. No.: 892,013

[22] Filed: Aug. 1, 1986

[30] Foreign Application Priority Data

Aug. 2, 1985 [JP] Japan .................................. 60-169693

[51] Int. Cl.$^4$ ................................................. C07F 9/12
[52] U.S. Cl. ..................................................... 549/222
[58] Field of Search ......................................... 549/222

[56] References Cited

FOREIGN PATENT DOCUMENTS 45-4497 2/1970 Japan .

Primary Examiner—Richard L. Raymond
Attorney, Agent, or Firm—Sughrue, Mion, Zinn, Macpeak & Seas

[57] ABSTRACT

A process of purifying L-ascorbic acid 2-phosphate is disclosed, comprising passing a solution containing L-ascorbic acid 2-phosphate through a column of a basic anion exchanger resin whose ion-exchange groups consist essentially of a primary amine group, a secondary amine group, a tertiary amine group or a mixture thereof, and eluting the L-ascorbic acid 2-phosphate with an aqueous solution of a mineral acid or an inorganic salt. L-ascorbic acid 2-phosphate can be isolated at a high efficiency through easy steps.

14 Claims, No Drawings

PROCESS FOR PURIFYING L-ASCORBIC ACID 2-PHOSPHATE

BACKGROUND OF THE INVENTION

This invention relates to a process for purifying L-ascorbic acid 2-phosphate, which is useful as a stable vitamin C source in various industrial fields, such as food, cosmetics, and the like.

BACKGROUND OF THE INVENTION

Known purification processes for L-ascorbic acid 2-phosphate include a process of using activated carbon as disclosed in Japanese Patent Application (OPI) Nos. 51293/84 and 106494/84 (the term "OPI" as used herein referred to a "published unexamined Japanese patent application"), a process of using a strongly acidic cation exchange resin and a process of using a strongly basic anion exchange resin (having a quaternary ammonium salt as ion-exchange group) of a bicarbonate ion type as disclosed in Japanese Patent Publication No. 4497/70, Examples 1 to 3.

The process of using activated carbon is satisfactory for removing trace amounts of colored substances but does not meet the purpose of removing by-products, e.g., L-ascorbic acid 3-phosphate, L-ascorbic acid 2-pyrophosphate, bis(L-ascorbic acid)phosphates, etc., and unreacted L-ascorbic acid. The process of using a strongly acidic cation exchange resin is used for removal of basic substances used in the reaction, but does not satisfactorily remove the above-described by-products and unreacted L-ascorbic acid. On the other hand, the ion exchange purification with a strongly basic ion exchange resin can provide pure L-ascorbic acid 2-phosphate. However, in order to achieve this purpose, the ion exchange resin should previously be converted into a bicarbonate ion type or a large quantity of a sodium bicarbonate aqueous solution is required as an eluent. As a result, there arise problems, such as remarkable foaming in the column, necessity of removal of sodium bicarbonate, and the like, which lead to serious disadvantages in an industrial application.

Thus, none of these known purification processes is satisfactory in terms of purification capacity or efficiency.

SUMMARY OF THE INVENTION

An object of this invention is to provide a process of isolating L-ascorbic acid 2-phosphate from a solution containing L-ascorbic acid 2-phosphate through easy and short steps in a large commercial scale.

The inventors have conducted intensive and extensive investigations to develop a process for purifying L-ascorbic acid 2-phosphate which eliminates the above-described disadvantages. As a result, it has now been found that the above object can be accomplished by purifying the above-described solution by using a weakly basic or medium-basic anion exchange resin. The present invention has been completed based on this finding.

This is, the present invention relates to a process of purifying L-ascorbic acid 2-phosphate which comprises passing a solution containing L-ascorbic acid 2-phosphate through a column of a basic anion exchange resin whose ion-exchange groups consist essentially of a primary amine group, a secondary amine group, a tertiary amine group or a mixture thereof, and then eluting L-ascorbic acid 2-phosphate from the column with an aqueous solution of a mineral acid or an inorganic salt.

DETAILED DESCRIPTION OF THE INVENTION

The solution containing L-ascorbic acid 2-phosphate to be purified by the process of this invention includes: (1) a reaction mixture obtained by subjecting L-ascorbic acid with its 5- and 6-positions being protected or unprotected (e.g., 5,6-isopropylideneascorbic acid) to esterification with a phosphorus oxyhalide as described in U.S. Pat. No. 4,179,445; (2) a solution obtained by desalting the reaction mixture of (1) above with a cation exchange resin, etc.; (3) a solution obtained by collecting crystals in the form of a salt from the reaction mixture of (1) above and treating a solution of the crystals with a cation exchange resin: and the like.

In particular, synthesis of L-ascorbic acid 2-phosphate directly from L-ascorbic acid with its 5- and 6-positions being unprotected is superior from the economical viewpoint, which comprises reacting L-ascorbic acid with a phosphorus oxychloride in water in the presence of a catalyst (e.g., pyridine) and a hydrogen chloride-removing agent (e.g., an alkali metal salt). However, this method encounters with difficulties in suppressing formation of by-products, particularly L-ascorbic acid 3-phosphate and L-ascorbic acid pyrophosphate which cannot be removed by crystallization (precipitation) step, while by-products, bis(L-ascorbic acid)phosphates can be easily removed by the crystallization step. However, the purification process according to the present invention makes it possible to remove L-ascorbic acid 3-phosphate and L-ascorbic acid pyrophosphate from such a reaction mixture with high efficiency.

The weakly basic or medium-basic anion exchange resin which can be used in the present invention has ion-exchange groups consisting essentially of a primary amine group, a secondary amine group, a tertiary amine group or a mixture thereof. It is preferred that the basic anion exchange resin have substantially no quaternary ammonium salt (not more than 15 mol% based on the total ion-exchange groups). Examples of the basic anion exchange resin include polystyrene resins crosslinked with e.g., divinylbenzene, etc., crosslinked acrylic resins and the like. The ion-exchange groups can be introduced into these resins in the form of alkylamines or polyamines such as polyethyleneimine and polyethylenediamine, or by polymerizing a monomer having an amino group. These resins may be gel type resins or macroporous type resins.

Specific examples of such anion exchange resins commercially available include Amberlite IRA-35 and IRA-68 (produced by Rohm & Haas Co.), Dowex 66 and WGR-2 (produced by Dow Chemical Co.), Diaion WA 10 and 20 (produced by Mitsubishi Chemical Industries. Ltd.), etc.

When the above-described solution is passed through a column packed with these anion exchange resins, L-ascorbic acid 2-phosphate, by-products (e.g., L-ascorbic acid 3-phosphate, L-ascorbic acid pyrophosphate, etc.) and the unreacted L-ascorbic acid in the solution are adsorbed onto the resin while other substances used in the reaction, such as organic solvents, bases, etc., pass through the column without being adsorbed.

The amount of the anion exchange resin to be used is usually at least equal to (preferably from about 3 to about 15 times) the equivalent of L-ascorbic acid 2-phosphate contained in the solution on ion exchange capacity basis.

The thus adsorbed L-ascorbic acid, L-ascorbic acid 2-phosphate and the by-products can be eluted with an aqueous solution of a mineral acid or an inorganic salt in the order listed.

Specific examples of the mineral acid or inorganic salt aqueous solution to be used as a developing solution include dilute hydrochloride acid, dilute sulfuric acid, an aqueous solution of phosphoric acid, sodium chloride, potassium chloride, calcium chloride, magnesium chloride, sodium sulfate or sodium hydrogenphosphate, and mixtures thereof.

L-ascorbic acid, L-ascorbic acid 2-phosphate and the by-products, i.e., L-ascorbic acid 3-phosphate and L-ascorbic acid pyrophosphate, can successively be effused by gradually increasing the concentration of the above-described developing solution. The rate of flow is so selected as to follow a commonly employed elution procedure. For example, the space velocity (the volume (l) of liquid flowing out for one hour per unit volume (l) of the ion exchange resin) usually ranges from about 0.1 to about 1.0 l/l.hr, and preferably from about 0.03 to about 3 l/l.hr.

Thus, an L-ascorbic acid 2-phosphate aqueous solution free from unreacted L-ascorbic acid and the by-products can be obtained. If desired, the resulting aqueous solution may be isolated in the form of an appropriate salt by subjecting to neutralization, (optionally concentration) and crystallization. For example, L-ascorbic acid 2-phosphate can be isolated in the form of an alkali metal or alkaline earth metal salt (e.g., a magnesium salt) by neutralizing the aqueous solution with an alkali metal or alkaline earth metal compound capable of forming a salt with L-ascorbic acid 2-phosphate (e.g., magnesium oxide, magnesium carbonate and magnesium hydroxide), removing the excessive alkali metal or alkaline earth metal compound, phosphate thereof, etc., e.g., by filtration, concentrating the resulting solution and crystallizing the concentrate from an alcohol.

According to the ion exchange purification process of the present invention, the desired product and the by-products once adsorbed onto the weakly basic or medium-basic anion exchange can be developed in fractions among which each of these components are sharply separated from each other by varying the concentration of a developing solution at a gradient within a relatively low concentration range. If in using a strongly basic anion exchange resin, the effluent peaks become broad, and increase in concentration of a developing solution results in unsharp separation among components as shown in Comparative Examples hereinafter given.

In the process of this invention, it is preferred to use the developing solutions having three levels of concentration; from 0.001 to 0.1 g equivalent/l for the first step to flow out L-ascorbic acid alone; from 0.03 to 0.3 g equivalent/l, but higher than that in the first step, for the second step to flow out L-ascorbic acid 2-phosphate without the by-products; and from 0.5 to 2 g equivalent/l for the third step to flow out the by-products. However, these preferred ranges vary depending on the kind of anion exchange resins used.

As described above, the purification process in accordance with the present invention makes it possible to markedly reduce the amount of effluent and the amount of an inorganic salt required for neutralization as compared with the use of strongly basic anion exchange resins, to thereby greatly improve efficiency in concentration and crystallization steps on an industrial scale. In addition, the process of the invention has an advantage that final products of high purity can be obtained through shorter steps since it is easy to avoid incorporation of inorganic salts into the products.

According to the present invention, L-ascorbic acid 2-phosphate can be isolated from a solution containing L-ascorbic acid 2-phosphate through easy and short steps even on an industrial scale by the use of a weakly basic or medium-basic anion exchange resin for purification. Therefore, the purification process of the present invention offers great advantages over the conventional processes in terms of reduction in both facilities and time required.

This invention will not be illustrated in greater detail with reference to the following examples, but it should be understood that they are not intended to limit the present invention.

EXAMPLE 1

Five grams (28.4 mmol) of L-ascorbic acid, 4.49 g of pyridine, 40 ml of water and 10 ml of tetrahydrofuran (THF) were mixed to form a solution. To the resulting solution, 5 ml of a THF solution containing 4.79 g of phosphorus oxychloride and 10 ml of an aqueous solution containing 7.85 g of potassium carbonate were simultaneously added dropwise at such dropping rates as to maintain at a temperature of from 0° to 10° C. The reaction mixture was diluted with water to a volume of 200 ml and adjusted to a pH of from 3.5 to 4 with hydrochloric acid. The solution was then passed through a column packed with 250 ml of a medium-basic anion exchange resin (a gel-type acrylic resin having a tertiary amine group as ion-exchange group; Amberlite IRA-68) pretreated with hydrochloric acid. The column was then developed with 1,000 ml of a 0.01N hydrochloric acid aqueous solution. The resulting effluent contained pyridine, potassium chloride, THF and the unreacted L-ascorbic acid. Then, the column was developed with 1,500 ml of 0.2N hydrochloric acid to obtain a fraction containing L-ascorbic acid 2-phosphate. High performance liquid chromatography (HPLC) of this fraction revealed that 92.3% of L-ascorbic acid 2-phosphoric (based on the total amount thereof produced by the reaction; hereafter the same) was contained therein, and that the total content of L-ascorbic acid 3-phosphate and L-ascorbic acid 2-pyrophosphate in this fraction was 0.81 wt% (based on the weight of L-ascorbic acid 2-phosphate contained therein; hereafter the same). Finally, the column was developed with 500 ml of 2N hydrochloric acid to obtain a fraction containing by-products.

EXAMPLE 2

Ten grams of crude crystals of L-ascorbic acid 2-phosphate magnesium salt (pure content: 23.9 mmol) containing 1.3 wt% of L-ascorbic acid and 8.0% of by-products were dissolved in 50 ml of water, and the aqueous solution was passed through a column packed with 200 ml of a strongly acidic cation exchange resin (a gel-type polystyrene resin having a sulfonic acid group as ion-exchange group; Amberlite IR-120B, H− type). The column was eluted with water to collect 250 ml of an effluent. The effluent was then passed through a column packed with 120 ml of a weakly basic anion exchange resin (a macroporous-type acrylic resin having a tertiary amine group as ion-exchange group; Amberlite IRA-35), followed by developing with 1,500 ml of an aqueous solution containing 0.01 mol/l of magnesium chloride. The effluent obtained here contained L-ascorbic acid only. Then, the column was developed with 2,200 ml of an aqueous solution containing 0.1 mol/l of magnesium chloride to obtain a fraction containing L-ascorbic acid 2-phosphate. HPLC analysis revealed that this fraction contained 22.2 mmol of L-ascorbic acid 2-phosphate, and that the total content of the by-products in this fraction was 0.83 wt%. The column was finally developed with an aqueous solution containing 1 mol/l of magnesium chloride to obtain a fraction containing the by-products.

COMPARATIVE EXAMPLE 1

The same reaction mixture as obtained in Example 1 was diluted with water to a volume of 200 ml. The resulting aqueous solution was passed through a column packed with 270 ml of a strongly basic anion exchange resin (a gel-type polystyrene resin having a quaternary ammonium salt as ion-exchange group; Amberlite IRA-402) and then eluted with 2,000 ml of 0.01N hydrochloric acid. The resulting effluent contained pyridine, potassium chloride, THF and L-ascorbic acid. The column was then developed with 1,500 ml of 0.2N hydrochloric acid, but the effluent contained only 42.3% of L-ascorbic acid 2-phosphate. When the development was further contained, 3,000 ml of 0.2N hydrochloric acid was required for obtaining 73.2% of L-ascorbic acid 2-phosphate. The amount of hydrogen chloride contained in the resulting 3,000 ml-fraction amount to 43 molar times the desired product (that in Example 1 was 15 times). Therefore, when this fraction is neutralized, followed by crystallization to obtain the product in the form of an appropriate salt, the amount of produced inorganic salt becomes too large to expect a high yield. Moreover, since a considerable amount of the inorganic salt is incorporated into the resulting crystal, a high pure product can never be obtained unless the crystal be subjected to an additional purification procedure, such as recrystallization.

In order to further elute the remaining L-ascorbic acid 2-phosphate, the column was finally developed with 1,000 ml of 0.3N hydrochloric acid. By this development, 14.8% of L-ascorbic acid 2-phosphate was additionally eluted out to obtain 88% in total, but, at the same time, the by-products were also eluted. The amount of the by-products eluted was 8.6% based on the total weight of L-ascorbic acid 2-phosphate eluted.

COMPARATIVE EXAMPLE 2

In the same manner as described in Example 2, 250 ml of an effluent from a column of IR-120B was prepared. The aqueous solution was passed through a column packed with 100 ml of a strongly basic anion exchange resin (Amberlite IRA-402), and the column was developed with 2,500 ml of an aqueous solution containing 0.01 mol/l of magnesium chloride. The resulting effluent contained L-ascorbic acid alone. When the column was then developed with 2,200 ml of an aqueous solution containing 0.1 mol/l of magnesium chloride, the effluent contained only 9.2 mmol of L-ascorbic acid 2-phosphate. When the development was further continued using the same developing solution, 3,500 ml of the developing solution was needed to obtain 14.1 mmol of the desired product.

The amount of magnesium chloride present in the resulting 3,500 ml-fraction amounted to 24 molar times the desired product (that in Example 2 was 9 times). Therefore, a high yield cannot be expected from crystallization of the product in the form of a magnesium salt. Further, since a large amount of magnesium chloride is incorporated into the crystal, a high pure product cannot be obtained unless the crystal is subjected to an additional purification procedure, such as recrystallization.

In order to further elute the remaining L-ascorbic acid 2-phosphate, the column was finally developed with 1,500 ml of an aqueous solution containing 0.2 mol/l of magnesium chloride. However, the resulting effluent was found to contain not only 2.9 mmol of the desired product (making 17.0 mmol in total) but also the undesired by-products.

While the invention has been described in detail and with reference to specific embodiments thereof, it will be apparent to one skilled in the art that various changes and modifications can be made therein without departing from the spirit and scope thereof.

What is claimed is:

1. A process of purifying L-ascorbic acid 2-phosphate which comprises passing a solution containing L-ascorbic acid 2-phosphate through a column of a basic anion exchange resin whose ion exchange groups consist essentially of a primary amine group, a secondary amine group, a tertiary amine group or a mixture thereof, and eluting the L-ascorbic acid 2-phosphate with an aqueous solution of a mineral acid or an inorganic salt.

2. A process as in claim 1, wherein said solution containing L-ascorbic acid 2-phosphate is obtained by esterification of unprotected L-ascorbic acid with a phosphorus oxyhalide.

3. A process as in claim 1, wherein said anion exchange resin is used in an amount at least equal to the equivalent of L-ascorbic acid 2-phosphate contained in the solution on ion exchange capacity basis.

4. A process as in claim 3, wherein said anion exchange resin is used in an amount from about 3 to about 15 times the equivalent of L-ascorbic acid 2-phosphate contained in the solution on ion exchange capacity basis.

5. A process as in claim 1, wherein unreacted L-ascorbic acid, L-ascorbic acid 2-phosphate and by-products are successively eluted by gradually increasing the concentration of said aqueous solution of a mineral acid or an inorganic salt.

6. A process as in claim 5, wherein said concentration is increased in three steps, and it is from 0.001 to 0.1 g equivalent/l for the first step to flow out L-ascorbic acid, from 0.03 to 0.3 g equivalent/l but higher than that in the first step for the second step to flow out L-ascorbic acid 2-phosphate, and from 0.5 to 2 g equivalent/l for the third step to flow out by-products.

7. A process as in claim 1, wherein said aqueous solution of a mineral acid or an inorganic salt is (1) a dilute hydrochloric acid aqueous solution, (2) a dilute sulfuric acid aqueous solution, (3) an aqueous solution of phosphoric acid, sodium chloride, potassium chloride, calcium chloride, magnesium chloride, sodium sulfate or sodium hydrogenphosphate, or mixtures thereof or (4) or mixtures thereof.

8. A process as in claim 1, wherein said anion exchange resin has substantially no quaternary ammonium salt groups.

9. A process as in claim 1, wherein the elute containing the L-ascorbic acid 2-phosphate is further subjected to neutralization, and crystallization.

10. A process as in claim 9, wherein said neutralization is carried out using an alkali metal or alkaline earth metal compound capable of forming a salt with L-ascorbic acid 2-phosphate, and said crystallization is carried out using an alcohol.

11. A process as in claim 10, wherein said alkali metal or alkaline earth metal compound is magnesium oxide, magnesium carbonate or magnesium hydroxide.

12. A process as in claim 1, wherein said solution containing L-ascorbic acid 2-phosphate is (1) a solution obtained by subjecting protected or unprotected L-ascorbic acid to esterification with a phosphorous oxyhalide, (2) a solution obtained by desalting the solution of (1) above with a cation exchange resin, or (3) a solution obtained by collecting crystals in the form of a salt from the solution of (1) above and treating a solution of the crystals with a cation exchange resin.

13. A process as in claim 1, wherein said solution containing L-ascorbic acid 2-phosphate contains at least one of L-ascorbic acid, L-ascorbic acid 3-phosphate and L-ascorbic acid 2-pyrophosphate.

14. A process as in claim 1, wherein said basic anionic exchange resin does not contain more than 15 mole % of quaternary ammonium salt groups based on the total ion-exchange groups present in said resin.

* * * * *